(12) United States Patent
Pagani et al.

(10) Patent No.: US 12,042,197 B2
(45) Date of Patent: Jul. 23, 2024

(54) SURGICAL SCREWDRIVER

(71) Applicant: MEDACTA INTERNATIONAL SA, Castel San Pietro (CH)

(72) Inventors: Luca Pagani, Castel San Pietro (CH); Marco Riva, Castel San Pietro (CH); Meinrad Fiechter, Castel San Pietro (CH); Francesco Siccardi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 275 days.

(21) Appl. No.: 17/415,619

(22) PCT Filed: Dec. 17, 2019

(86) PCT No.: PCT/IB2019/060887
§ 371 (c)(1),
(2) Date: Jun. 17, 2021

(87) PCT Pub. No.: WO2020/128810
PCT Pub. Date: Jun. 25, 2020

(65) Prior Publication Data
US 2022/0079646 A1 Mar. 17, 2022

(30) Foreign Application Priority Data
Dec. 20, 2018 (IT) .................. 102018000020350

(51) Int. Cl.
*A61B 17/88* (2006.01)
*A61B 17/00* (2006.01)
(Continued)

(52) U.S. Cl.
CPC ........ *A61B 17/8888* (2013.01); *B25B 13/481* (2013.01); *B25B 15/008* (2013.01);
(Continued)

(58) Field of Classification Search
CPC ............ A61B 17/8875; A61B 17/1631; A61B 17/1613; A61B 17/808; A61B 17/8872;
(Continued)

(56) References Cited

U.S. PATENT DOCUMENTS 1,392,220 A 9/1921 Quint
5,797,918 A 8/1998 McGuire et al.
(Continued)

FOREIGN PATENT DOCUMENTS

JP 2003019142 A 1/2003

OTHER PUBLICATIONS

Examination Report No. 2 received in connection with Australian Application No. 2019409329, dated Sep. 16, 2022, 4 pages.
(Continued)

*Primary Examiner* — Marcela I. Shirsat
(74) *Attorney, Agent, or Firm* — Meunier Carlin & Curfman LLC

(57) ABSTRACT

Various implementations include a surgical screwdriver that comprises a first rotating shaft configured to be rotated about a respective longitudinal axis, a second rotating shaft extending along a respective development axis transverse to the longitudinal axis of the first shaft and having a shaped end tip that can be inserted into the head of a screw, and a transmission member interposed between respective first ends of the shafts to transfer the rotation from the first shaft to the second shaft. The transmission member comprises a pair of hemispherical elements, hinged together about a respective junction axis that is perpendicular to the longitudinal axis of the first shaft, and each hemispherical element is in turn hinged to a first end of one of said shafts.

14 Claims, 7 Drawing Sheets

(51) Int. Cl.
    *A61B 17/16*     (2006.01)
    *A61B 17/29*     (2006.01)
    *A61B 17/70*     (2006.01)
    *A61B 17/80*     (2006.01)
    *A61B 90/00*     (2016.01)
    *A61C 1/18*     (2006.01)
    *B25B 9/00*     (2006.01)
    *B25B 13/10*     (2006.01)
    *B25B 13/48*     (2006.01)
    *B25B 13/50*     (2006.01)
    *B25B 15/00*     (2006.01)
    *B25B 23/00*     (2006.01)
    *B25B 23/142*     (2006.01)

(52) U.S. Cl.
    CPC ............ *B25B 23/0014* (2013.01); *A61B 2017/00367* (2013.01); *A61B 2017/00424* (2013.01); *A61B 17/1624* (2013.01); *A61B 17/1631* (2013.01); *A61B 2017/2905* (2013.01); *A61B 17/7082* (2013.01); *A61B 17/808* (2013.01); *A61B 17/8872* (2013.01); *A61B 17/8875* (2013.01); *A61B 2090/031* (2016.02); *A61C 1/186* (2013.01); *B25B 9/00* (2013.01); *B25B 13/107* (2013.01); *B25B 13/505* (2013.01); *B25B 15/00* (2013.01); *B25B 23/0007* (2013.01); *B25B 23/0035* (2013.01); *B25B 23/1427* (2013.01)

(58) Field of Classification Search
CPC ............ A61B 17/1624; A61B 17/8888; A61B 17/1622; A61B 17/7082; A61B 2017/2905; A61B 2017/0046; A61B 2090/031; B25B 13/481; B25B 13/488; B25B 13/505; B25B 13/107; B25B 15/00; B25B 15/02; B25B 15/005; B25B 23/0007; B25B 23/0042; B25B 23/0014; B25B 23/0028; B25B 23/1427; B25B 23/0035; B25B 23/00; B25B 23/108; B25B 23/103; B25B 23/08; B25B 23/02; B25B 17/02; B25B 27/0042; B25B 27/00; B25B 27/023; B25B 9/00; B25B 21/007; B25G 1/063; B25G 1/005; B25G 1/025; B25G 1/06; B25G 1/043; B25G 1/066; B25G 1/04; B25G 1/00; B25G 1/02; B25F 5/02; A61C 1/186; A61C 1/18; A61C 1/185; A61C 8/0089
USPC ..... 606/104; 81/52, 53.1, 478, 57.26, 57.27, 81/57.29, 57.43, 64, 177.6
See application file for complete search history.

(56) References Cited

U.S. PATENT DOCUMENTS

| | | | |
|---|---|---|---|
| 2001/0021853 A1* | 9/2001 | Heckele | A61F 2/4611 606/104 |
| 2002/0007704 A1 | 1/2002 | Hahn | |
| 2011/0197719 A1* | 8/2011 | Neitzell | B25F 5/001 81/177.75 |
| 2012/0109142 A1* | 5/2012 | Dayan | B25B 23/08 606/104 |
| 2014/0018815 A1* | 1/2014 | Kirschman | A61F 2/4611 606/99 |
| 2014/0018816 A1 | 1/2014 | Fenn et al. | |
| 2018/0325574 A1 | 11/2018 | Bjork et al. | |
| 2022/0054178 A1 | 2/2022 | Pagani et al. | |

OTHER PUBLICATIONS

International Search Report and Written Opinion, issued by the International Searching Authority (ISA/EP) in PCT Application No. PCT/IB2019/060887 on Apr. 1, 2020. 13 pages.

International Search Report and Written Opinion, issued by the International Searching Authority (ISA/EP) in PCT Application No. PCT/IB2019/060892 on Apr. 1, 2020. 13 pages.

Non-Final Office Action received in connection with U.S. Appl. No. 17/415,613, dated Aug. 24, 2023, 10 pages.

Final Office Action for U.S. Appl. No. 17/415,613 dated Jan. 24, 2024.

* cited by examiner

SURGICAL SCREWDRIVER

TECHNICAL FIELD

The present invention relates to a surgical screwdriver, in particular one with a tilted axis, used to operate on screws or other threaded elements that attach to bone tissue.

PRIOR ART

Surgical screwdrivers are used to screw/unscrew clamping screws in various applications such as anterior interbody arthrodesis, where it is necessary to bind appropriate inserts to the vertebrae using the above-mentioned clamping screws.

In this specific case, the operator pierces the patient's skin by making an incision of just a few centimetres in order to insert the surgical tools, including the screwdriver.

In order to carry out an operation that is as minimally invasive as possible, therefore, the screwdrivers and other tools are kept coincident with the axis of the hole defined by the incision, i.e. with their development axis perpendicular to the surface on which the incision is made.

In this situation, in fact, the screwdriver must not be tilted in order to avoid widening the incision and, thus, tearing the skin tissue.

However, the clamping screws may have their own rotation axis, at the respective application site, that does not coincide with the axis of the hole defined by the incision.

In this situation, tilted-axis surgical screwdrivers are used and equipped with a longitudinal rod from which a shaped tip extends that is designed be inserted into the head of the screw and extending transversely to the rod.

In particular, the rod has a first end that is intended to remain outside the patient's body and on which the operator transmits the rotational motion. On the opposite side of the first end, a second end of the rod extends and is rotatably engaged with the shaped tip.

Between the second end of the rod and the shaped tip, a joint, typically a cardan joint, extends, which is capable of transferring the rotational motion of the rod to the shaped tip.

In particular, the joint consists of a first fork extending from the second end of the rod and a second fork from which the shaped tip extends. The forks are mutually pivoted using a cross-shaped element that enables the connection of the forks and the possibility of staggering the tip with respect to the rod.

In this way, the joint allows the rod to be kept aligned with the incision hole and, at the same time, to operate by screwing/unscrewing the screw positioned along an axis that is tilted with respect to the longitudinal extension of the rod itself.

The surgical screwdrivers described above, although capable of transferring the rotational motion between two transverse axes (rod axis and shaped tip axis), have, in any case, significant drawbacks.

A first, significant drawback is the transmission ratio between the rod and the shaped tip. It is well known that in this type of transmission the instantaneous angular velocity of the shaped tip (driven shaft) is not constant during a complete rotation but is a function of the misalignment angle of the shaped tip (driven shaft) axis with respect to the shaft axis (drive shaft). As the angle of incidence increases, the amplitude of oscillation of the angular velocity also increases.

There is, therefore, a non-fluid transmission between the rod and the shaped tip, which can generate vibrations and, during the operation on the screw, misalign the shaped tip with respect to the screw head. In this context, it is particularly uncomfortable for the operator to operate precisely and efficiently on the clamping screws.

Another significant drawback of the prior art described above is the overall dimensions of the cardan joint. In this context, it is very difficult to insert the screwdriver through small incisions. The presence of the two forks connected to each other means, in fact, that the screwdriver is considerably enlarged in a direction transverse to the longitudinal extension of the rod. For this reason, in order to enable the complete insertion of the joint, the surgical operator cannot keep the incision very small.

Finally, a further drawback, which is again linked to the presence of the cardan joint, is the presence of projecting elements that, in certain applications, may inadvertently interfere with the tissues surrounding the clamping screw.

In this case, in fact, the two forks of the cardan joint cause transverse projections that, during rotation, may engage the soft tissues close to the operating site and damage them.

The purpose of the present invention is, therefore, to make a surgical screwdriver available that overcomes the drawbacks of the prior art described above.

A first purpose of the present invention, in fact, is to propose a surgical screwdriver with a tilted axis capable of transmitting, in an almost constant way, the angular velocity transmitted by the surgeon, therefore ensuring a stable and precise operation on the clamping screw.

An additional purpose of the present invention is to propose a surgical screwdriver of limited dimensions in cross-section, in order to make the surgical operation as non-invasive as possible.

Finally, one purpose of the present invention is to propose a surgical screwdriver with tilted axes and equipped with a compact transmission joint without any roughness or projections that could interfere with the soft tissues surrounding the operating site.

These and other purposes are substantially attained by a surgical screwdriver, in particular with a tilted axis according to what is described in one or more of the accompanying claims.

SUMMARY

In particular, according to a first aspect, the present invention concerns a surgical screwdriver comprising a first rotating shaft configured to be rotated about a respective longitudinal axis and a second rotating shaft extending along a respective development axis and presenting a shaped end tip that can be inserted into the screw head. A transmission member is also provided interposed between the respective first shaft ends to transfer the rotation from the first shaft to the second shaft. The transmission member advantageously comprises a pair of hemispherical elements, mutually hinged to a respective junction axis perpendicular to the longitudinal axis of the first shaft; each hemispherical element being in turn hinged to a first end of one of said shafts.

A first hemispherical element preferably comprises a spherical dome-shaped surface sliding on an arched guide obtained in said first end of the first shaft. A second hemispherical element comprises a spherical dome-shaped surface sliding on an arched guide obtained in said first end of the second shaft.

The spherical dome-shaped surface of each hemispherical element preferably has an arched groove engaged in the respective arched guide to slide with respect to it. The hemispherical elements are advantageously hinged to the respective shafts about mutually parallel axes that are perpendicular to the longitudinal axis of the first shaft and to the junction axis.

The arched guide is preferably defined by a "C"-shaped surface obtained in the first ends of each shaft.

The first hemispheric element preferably comprises a semi-cylindrical portion having a side surface extending coaxially to said junction axis. The semi-cylindrical portion is arranged on the opposite side of the spherical dome-shaped surface.

The second hemispherical element preferably comprises a cavity counter-shaped to the semi-cylindrical portion and obtained on the opposite side to the spherical dome-shaped surface. The cylindrical portion is inserted into said cavity to make the hemispherical elements mutually rotatable and rotatable about the junction axis.

In accordance with a second aspect of the present invention, the first hemispherical element should comprise a projecting portion on the opposite side to the spherical dome-shaped surface and the second hemispherical element should comprise a fork projecting one the opposite side to the spherical dome-shaped surface. The projecting portion is rotatably coupled to said fork.

The projecting portion is preferably pivoted inside the fork to make the hemispherical elements mutually rotatable and rotatable about the junction axis.

The first end of the second shaft is preferably arranged on the opposite side to the shaped tip and the first shaft comprises a second end opposite the first for being engaged by a manual or automatic rotation actuator.

The screwdriver preferably also comprises an internally hollow cylindrical sleeve to accommodate at least part of said shafts and said transmission member. The second end of the first shaft projects outside a first sleeve opening. The shaped tip of the second shaft projects outside a second sleeve opening opposite the first opening.

The sleeve openings are preferably not mutually coaxial, the second opening defining the development axis of the second shaft transverse to the longitudinal axis of the first shaft.

The sleeve preferably comprises a projection defining a spherical outer surface for accommodating said transmission member; said second sleeve opening being obtained in the outer surface of the projection.

The first shaft preferably comprises two portions coaxially joined to each other inside the sleeve. The second end of the first shaft is obtained in one of said portions distal to the second shaft.

The sleeve preferably comprises an ergonomic portion arranged on an outer surface of the sleeve near the second end of the first shaft. The shafts are advantageously rotatable inside the sleeve around their respective axes and with respect to the sleeve itself.

Additional features and advantages will emerge in greater detail in the description of a preferred, but not exclusive, embodiment of a surgical screwdriver, according to the present invention and the dependent claims.

BRIEF DESCRIPTION OF THE DRAWINGS

The present invention will be made clearer by the following detailed description, with reference to the attached drawings provided by way of example only, wherein.

DETAILED DESCRIPTION

Figure 1:
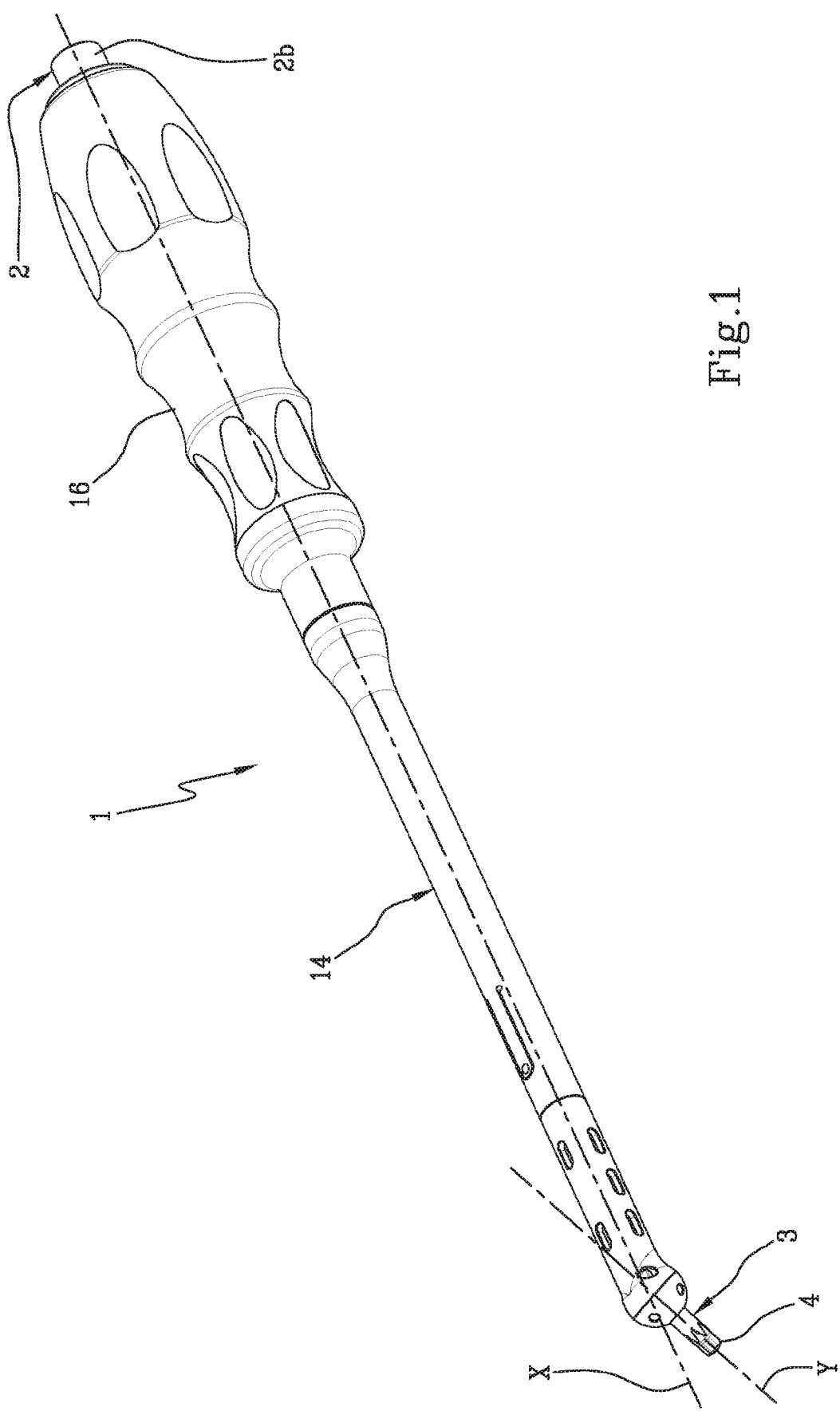
FIG. 1 shows a perspective view of a surgical screwdriver in accordance with the present invention.

In the above figures, the reference number 1 designates, in its entirety, a surgical screwdriver, according to the present invention.

The surgical screwdriver 1 is of the fixed tilted-axis type. In this case, in fact, as will be better clarified later in this discussion, the angle of incidence between the screwing operating axis and the motion actuation axis is predetermined and preferably 35°.

In more detail, the surgical screwdriver 1 comprises a first rotating shaft 2 configured to be rotated about a respective longitudinal extension axis "X".

The first shaft 2 can be rotated manually by the surgical operator, or using appropriate electromechanically controlled motorized systems.

The first shaft 2, made in the form of a stem, defines the "input" axis of the rotational motion and, in use, is kept coincident with the incision made in the patient.

The screwdriver 1 also comprises a second rotating shaft 3 extending along a respective development axis "Y" that is transverse to the longitudinal axis "X" of the first shaft 2. The second shaft 3 has a shaped end tip 4 to insert into the screw head (not shown in the attached figures as it is not part of the present invention).

The end tip 4 can have any shape (slotted, cross-shaped, or Allen-shaped, for instance) depending on the seat obtained in the screw head or other threaded member to be screwed/unscrewed. In the attached figures a Torx-type shaped tip 4, configured, therefore, in the shape of a six-pointed star, is shown for purely illustrative, non-limiting, purposes.

The development axis "Y" of the second shaft 3 therefore defines an "output" axis of the rotational motion and, in use, is arranged coaxially to the longitudinal extension of the screw in order to operate on the screw itself.

Between the first and second shaft 2, 3, there is also a transmission member 5, which is designed to transfer the rotation from the first shaft 2 to the second shaft 3.

The transmission member 5 is preferably interposed between respective first ends 2a, 3a, of the shafts 2, 3, opposite, respectively, the second end 2b of the first shaft 2 and the shaped tip 4 of the second shaft 3.

Figure 3:
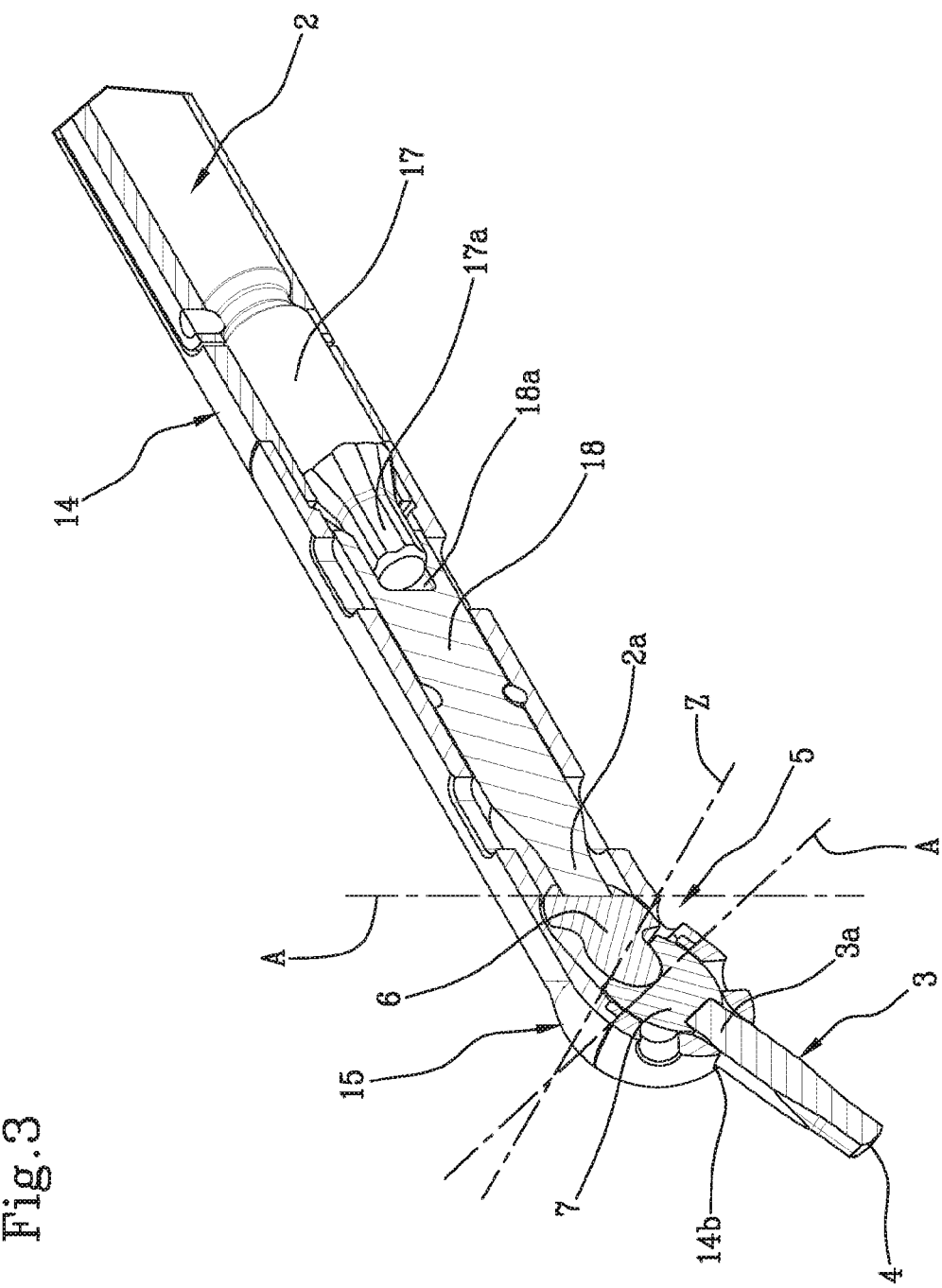
FIG. 3 is an enlarged view of a construction detail of the screwdriver shown in FIG. 2.
Figure 6:
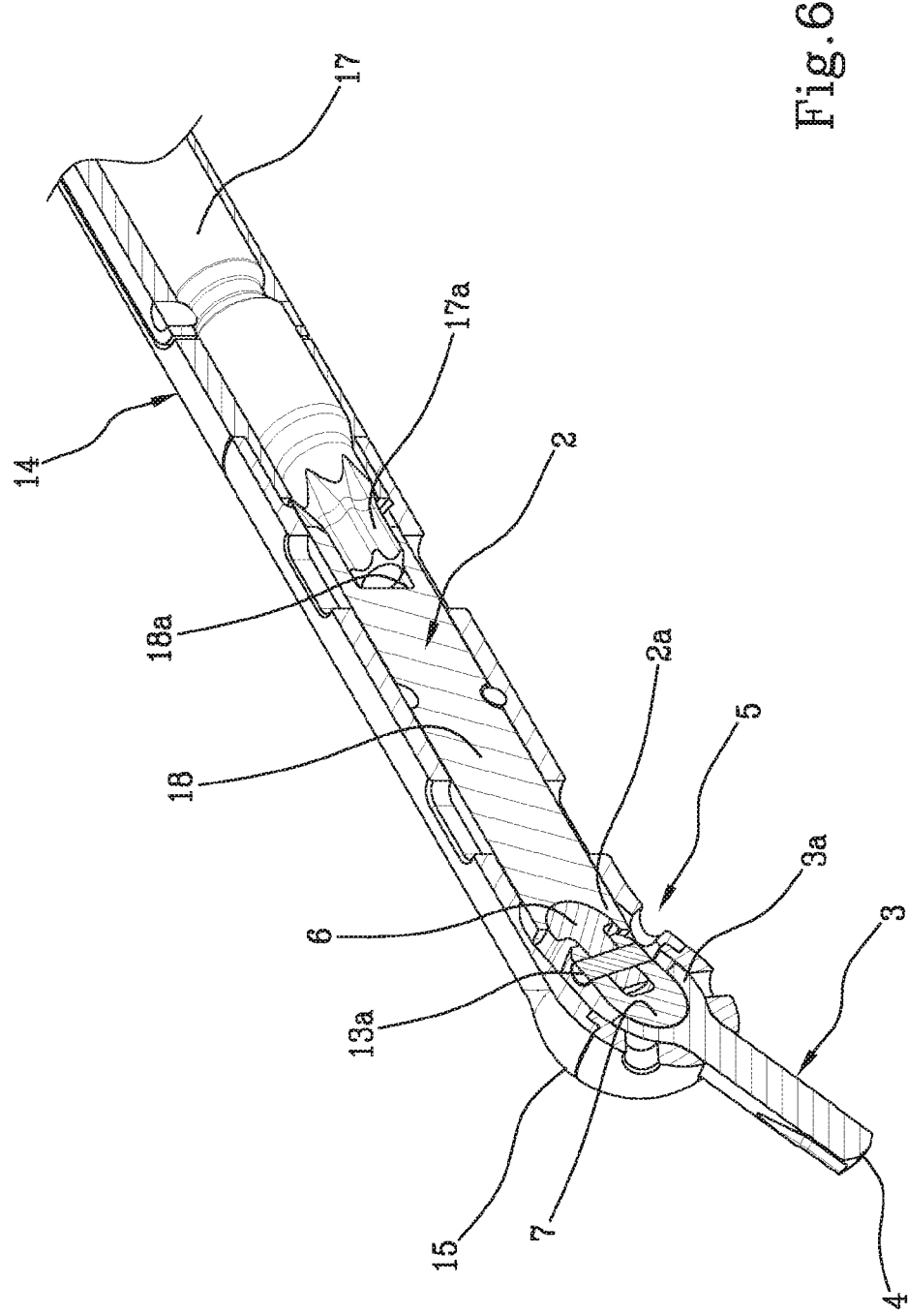
FIG. 6 is an enlarged view of a construction detail of the screwdriver shown in FIG. 5.

The transmission member 5 advantageously comprises a pair of hemispherical elements 6, 7 mutually hinged about a respective junction axis "Z" perpendicular to the longitudinal axis "X" of the first shaft 2 (FIGS. 3 and 6). Each hemispherical element 6, 7 is in turn hinged to a first end 2a, 3a of a respective shaft 2, 3.

The transmission member 5 defines a homokinetic joint, which is therefore able to keep the transmission ratio between the first shaft 2 (input axis) and the second shaft 3 (output axis) constant.

Figure 4:
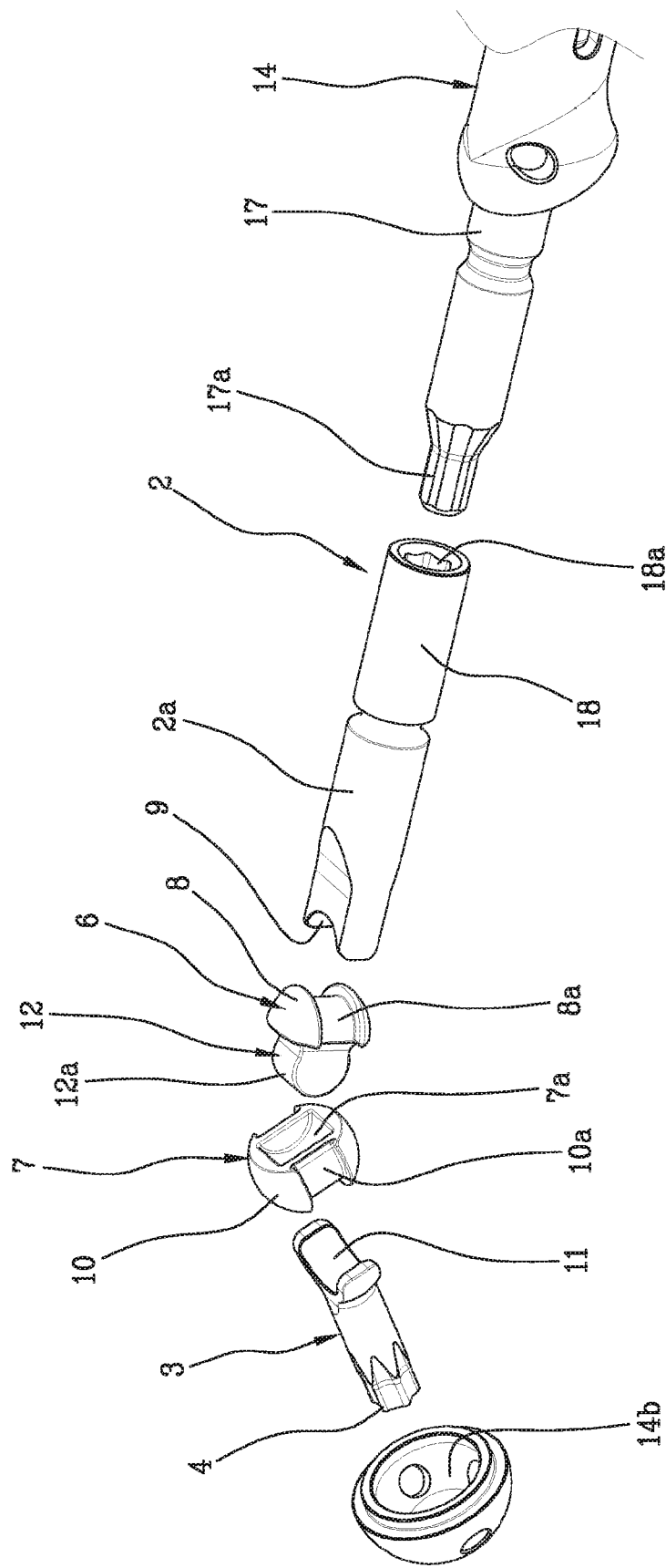
FIG. 4 shows an exploded perspective view of the construction detail highlighted in FIG. 3.
Figure 7:
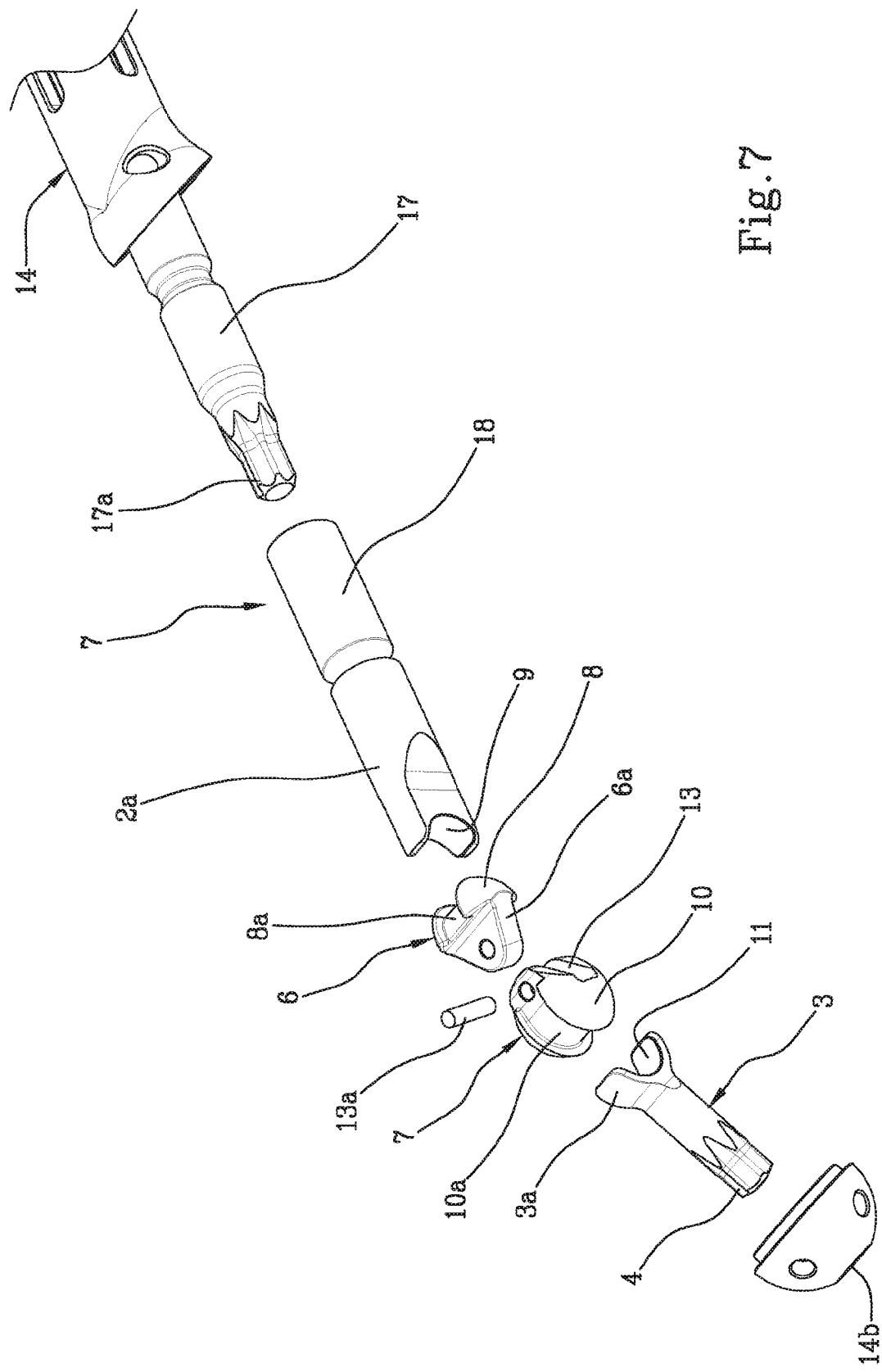
FIG. 7 shows an exploded perspective view of the construction detail highlighted in FIG. 6.

More specifically, as better shown in FIGS. 4 and 7, a first hemispherical element 6 comprises a spherical dome-shaped surface 8 sliding on an arched guide 9 obtained in the first end 2a of the first shaft 2. Similarly, a second hemispherical element 7 comprises a spherical dome-shaped surface 10 sliding on an arched guide 11 obtained in the first end 3a of the second shaft 3.

Each spherical dome-shaped surface 8, 10 of each hemispherical element 6, 7 advantageously has an arched groove 8a, 10a engaged to the respective arched guide 9, 11 to slide with respect to it.

In this situation, each arched guide 9, 11 is defined by a "C"-shaped surface obtained in the first ends 2a, 3a of each shaft 2, 3.

The hemispherical elements 6, 7 are advantageously hinged to the respective shafts 2, 3 about mutually parallel axes "A" perpendicular to the longitudinal axis "X" of the first shaft and to the junction axis "Z" (FIG. 3). In other words, the coupling between the hemispherical elements 6, 7 and between the shafts 2, 3 and the respective element 6,7 defines a three-axis joint, respectively the two parallel axes "A" and the junction axis "Z".

Figure 2:
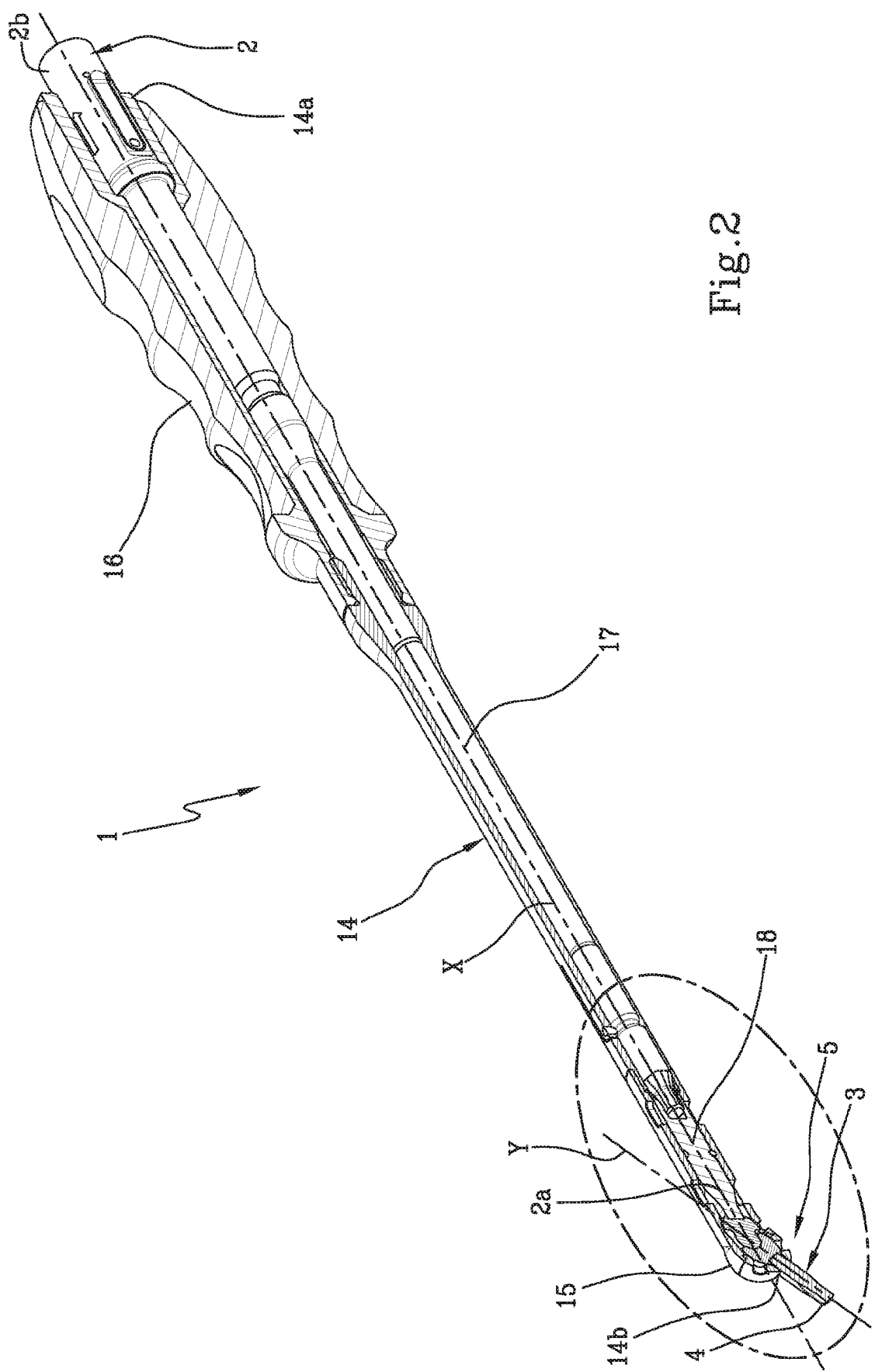
FIG. 2 shows a perspective view in partial longitudinal section of a first embodiment of the surgical screwdriver shown in FIG. 1.

In accordance with the first embodiment shown in FIGS. 2 to 4, the first hemispheric element 6 comprises a semi-cylindrical portion 12 having a side surface 12a extending coaxially to the above-mentioned junction axis "Z". The semi-cylindrical portion 12 extends on the opposite side to the spherical dome-shaped surface 8.

In this situation, the second hemispheric element 7 comprises a cavity 7a counter-shaped to the semi-cylindrical portion 12 and obtained on the opposite side to the spherical dome-shaped surface 10.

The semi-cylindrical portion 12 is advantageously inserted into the cavity 7a to make the hemispherical elements 6, 7 mutually rotatable and rotatable about the junction axis (Z).

Figure 5:
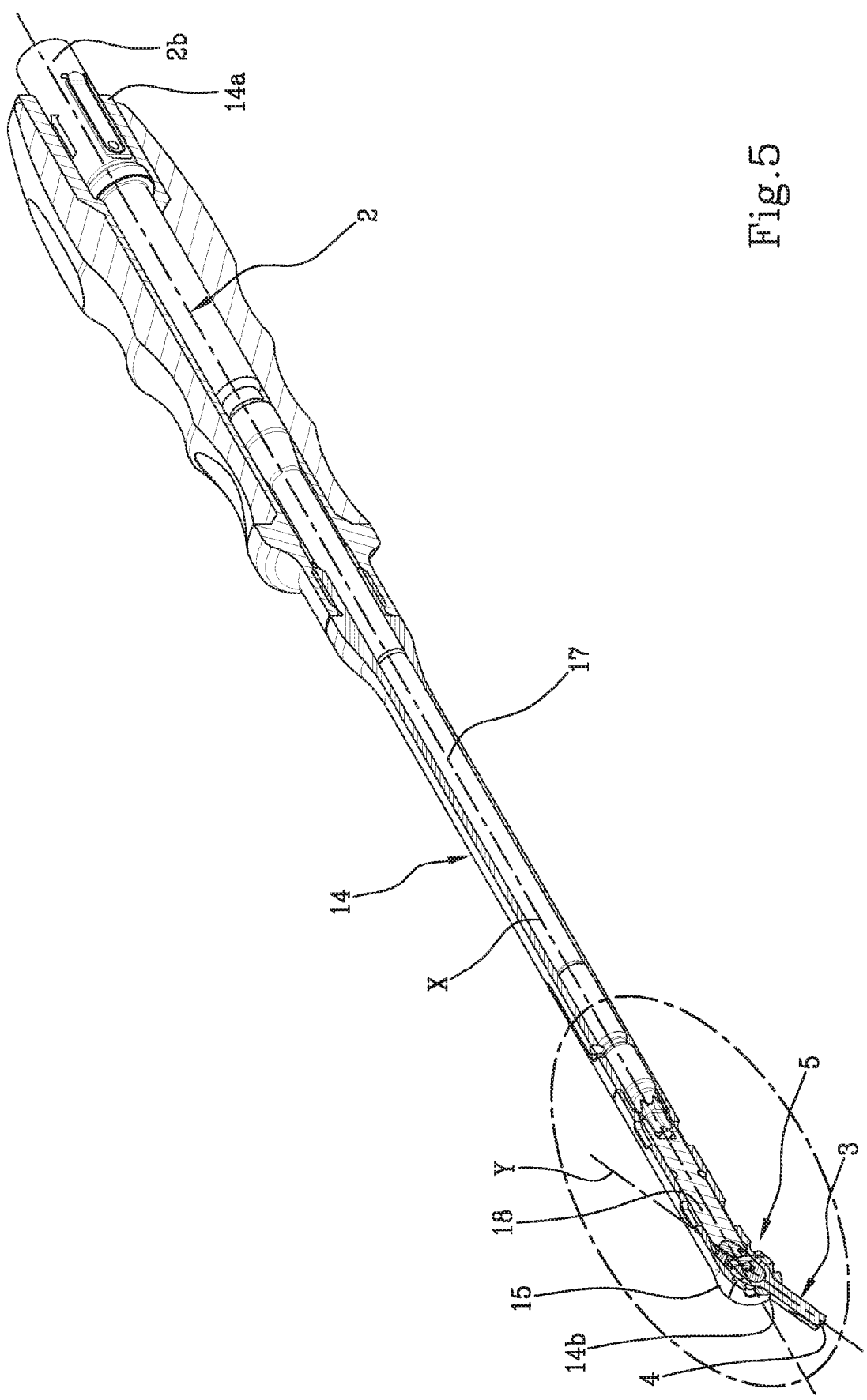
FIG. 5 shows a perspective view in partial longitudinal section of a second embodiment of the surgical screwdriver shown in FIG. 1.

In accordance with a second embodiment shown in FIGS. 5 to 7, the first hemispherical element 6 comprises a projecting portion 6a on the opposite side to the spherical dome-shaped surface 8 and equipped with a through hole.

In this situation, the second hemispherical element 7 comprises a fork 13 projecting on the opposite side to the spherical dome-shaped surface 10.

The projecting portion 6a is advantageously rotatably coupled to the fork 13.

More specifically, the projecting portion 6a is pivoted inside the fork 13 to make the hemispherical elements 6, 7 mutually pivoted about the junction axis "Z". A pin 13a is preferably provided extending along the junction axis "Z" and can be inserted through the fork and the hole of the projecting portion 6a.

It should also be noted that, for both the embodiments described above, the first end 3a of the second shaft 3 is arranged on the opposite side to the shaped tip 4, while the second end 2b of the first shaft 2 is configured so that it can be engaged by a manual or automatic rotation actuator.

In this way, the hemispherical elements 6, 7 are bound in rotation (about the axes "X", "Y" of the respective shafts 2, 3) but free to relatively slide to keep the transverse angle of incidence (e.g. at 35° in this embodiment) between the two axes "X", "Y".

The screwdriver 1 may also comprise an internally hollow cylindrical sleeve 14, which has a tubular shape and extends along the longitudinal axis "X" of the first shaft 2.

In particular, the sleeve 14 accommodates the transmission member 5 and, at least partially, the shafts 2, 3.

In this situation, the second end 2b of the first shaft 2 projects outside a first opening 14a of the sleeve 14. This second end 2b is handled by the operator to actuate the rotation of the first shaft 2 or is engaged in torque limiters or other appropriate transmission and/or motorization systems (not shown as they are not part of the present invention).

In addition, the shaped tip 4 of the second shaft 3 also projects outside a second opening 14b of the sleeve 14 opposite to the first opening 14a and opposite to the second end 2b of the first shaft 2.

In this situation, it should be noted that the openings 14a, 14b of the sleeve 14 are not mutually coaxial, but staggered to define the angle of incidence between the "X, Y" axes.

In fact, the second opening 14b defines the orientation of the development axis "Y" of the second shaft 3, binding this position with respect to the longitudinal axis "X" of the first shaft.

In use, keeping the sleeve 14 fixed, it is possible to rotate the first shaft 2 and therefore also the shaped tip 4, using the transmission member 5 placed inside the sleeve 14 itself.

It should also be noted that the sleeve 14 comprises a projection 15 defining a spherical outer surface for accommodating the entire member 5 consisting of the elements 6, 7. The projection 15 preferably consists of two hemispheres that can be mutually coupled as highlighted in the exploded view in FIGS. 4 and 7.

The second opening 14b of the sleeve 14 is obtained in the outer surface of the projection 15.

It should be noted that only the shaped tip 4 projecting from the sleeve 14 is the only rotating member inside the patient's body. All the rotating members (the shafts 2, 3 and the elements 6, 7) are advantageously protected inside the sleeve 14. In this situation, it should also be noted that the second end 2b of the first shaft 2 remains outside the patient's body.

Again, to hold the screwdriver 1 in place, an ergonomic portion 16 is provided that is obtained in the outer surface of the sleeve 14 near the second end 2b of the first shaft 2.

The ergonomic portion 16 enables you to manually hold the sleeve with respect to the incision and with respect to the patient, and, at the same time, to unscrew/screw the screw by operating on the first shaft 2.

The first shaft 2 is preferably made of two portions 17, 18 coaxially joined to each other inside the sleeve 14 and made in the form of respective rods.

In this situation, the second end 2b of the first shaft 2 is obtained in a first portion 17 distal from the second shaft 3.

The first portion 17 also has a shaped pin 17a, which can be reversibly joined to a respective shaped seat 18a of the second portion 18.

In turn, the second portion 18 has, on the opposite side of the shaped seat 18a, the arched guide 9 that is "C"-shaped.

The first portion 17 is held manually inside the sleeve 14 and pushed against the second portion 18 to define the coupling between the pin 17a and the seat 18, which guarantees the transmission of the rotation between the first and second portion 17, 18.

The first portion 17 can advantageously be removed from the sleeve 14 and possibly replaced with other functionally equivalent rods.

The screwdriver 1 described above overcomes the drawbacks of the prior art and entails important advantages.

First of all, the transmission member 5 defines a homokinetic joint that enables the transmission ratio between the angular velocity of the first shaft 2 and the second shaft 3 to be kept constant.

This advantage is derived from the structure of the two elements 6, 7 that form, when mutually coupled and with their respective axes 2, 3, three hinges that can rotate about the two axes "A" and about the common junction axis "Z".

The rotational movement is, advantageously, more homogeneous, smooth, and, therefore, more precise during the tightening of the screws.

A further significant advantage is the very small overall size, especially in the positioning area of the transmission member 5.

This advantage is due to the shape of the two hemispherical elements 6, 7, which enable a considerable reduction in its overall size compared to the known cardan joints.

The surgical operator can, advantageously, make an incision of a very limited size, thus facilitating the minimum invasiveness of the operation.

Finally, another important advantage of the present invention is due to the absence of projecting portions that, when rotating, can interfere with the tissues surrounding the clamping screws.

It should be noted, in particular, that the transmission member 5 is always contained inside the sleeve 14 and, therefore, there is no risk of direct contact with this moving part and the soft tissues. In addition, the presence of spherical surfaces and, therefore, the absence of outer edges, eliminates any possible damage to the soft tissues resulting from unintentional contact between the screwdriver 1 and the tissues themselves.

The invention claimed is:

1. A surgical screwdriver comprising:
a first rotating shaft configured to be rotated about a respective longitudinal axis;
a second rotating shaft extending along a respective development axis and having a shaped end tip which can be inserted into the head of a screw; and
a transmission member interposed between respective first ends of the rotating shafts,
wherein said transmission member comprises a pair of first and second hemispherical elements hinged together about a junction axis which is perpendicular to the longitudinal axis of the first rotating shaft, wherein the first and second hemispherical elements are hinged together so as to transfer rotation from the first rotating shaft to the second rotating shaft, and
wherein the first hemispherical element is hinged to the first end of the first rotating shaft and the second hemispherical element is hinged to the first end of the second rotating shaft so as to define a three-axis joint about which the first and second rotating shafts pivot relative to each other.

2. The screwdriver according to claim 1, wherein the first hemispherical element of the pair of hemispherical elements comprises a spherical dome-shaped surface sliding on an arched guide obtained in said first end of the first rotating shaft, and the second hemispherical element of the pair of the hemispherical elements comprises a spherical dome-shaped surface sliding on an arched guide obtained in said first end of the second rotating shaft.

3. The screwdriver according to claim 2, wherein said spherical dome-shaped surface of each hemispherical element has an arched groove engaged with the respective arched guide to slide with respect thereto, said hemispherical elements being hinged to the respective rotating shafts about mutually parallel axes which are perpendicular to the longitudinal axis of the first rotating shaft and to the junction axis.

4. The screwdriver according to claim 2, wherein said arched guide is defined by a "C-shaped" surface obtained in the first ends of each rotating shaft.

5. The screwdriver according to claim 2, wherein said first hemispherical element comprises a semi-cylindrical portion having a side surface extending coaxially with said junction axis, said semi-cylindrical portion being arranged on an opposite side of the first hemispherical element with respect to the spherical dome-shaped surface.

6. The screwdriver according to claim 5, wherein said second hemispherical element comprises a cavity which is counter-shaped with respect to the semi-cylindrical portion and obtained on an opposite side of the second hemispherical element with respect to the spherical dome-shaped surface, said semi-cylindrical portion being inserted into said cavity to make the hemispherical elements mutually rotatable and rotatable about the junction axis.

7. The screwdriver according to claim 2, wherein said first hemispherical element comprises a projecting portion on an opposite side of the first hemispherical element with respect to the spherical dome-shaped surface of the first hemispherical element and said second hemispherical element comprises a fork projecting from an opposite side of the second hemispherical element with respect to the spherical dome-shaped surface of the second hemispherical element, said projecting portion being rotatably coupled to said fork.

8. The screwdriver according to claim 7, wherein said projecting portion is pivoted inside the fork to make the hemispherical elements mutually rotatable and rotatable about the junction axis.

9. The screwdriver according to claim 1, wherein said first end of the second rotating shaft is arranged on an opposite side of the second rotating shaft with respect to the shaped end tip and in that said first rotating shaft comprises a second end opposite to the first end of the first rotating shaft to be engageable by a manual or automatic rotation actuator.

10. The screwdriver according to claim 9 wherein the screwdriver further comprises a cylindrical sleeve which is internally hollow to accommodate at least partially said first and second rotating shafts and said transmission member, said second end of the first rotating shaft projecting out of a first opening of the sleeve, said shaped end tip of the second rotating shaft projecting out of a second opening of the sleeve opposite to the first opening.

11. The screwdriver according to claim 10, wherein said openings of the sleeve are not coaxial with each other, said second opening defining the development axis of the second rotating shaft transverse to the longitudinal axis of the first rotating shaft.

12. The screwdriver according to claim 10, wherein said sleeve comprises a projection defining a spherical outer surface for accommodating said transmission member, said second opening of the sleeve being obtained on the outer surface of the projection.

13. The screwdriver according to claim 10, wherein said first rotating shaft comprises two portions coaxially associated with each other inside the sleeve, said second end of the first rotating shaft being obtained in one of said portions which is distal from the second rotating shaft.

14. The screwdriver according to claim 10, wherein said sleeve comprises an ergonomic portion arranged on an outer surface of the sleeve which is close to the second end of the first rotating shaft, said rotating shafts being rotatable inside the sleeve about their respective axes and with respect to the sleeve itself.

* * * * *